US00PP29324P2

(12) United States Plant Patent
van Straaten et al.

(10) Patent No.: US PP29,324 P2
(45) Date of Patent: May 29, 2018

(54) **VARIETY OF *HYDRANGEA* PLANT NAMED 'STRABRU'**

(50) Latin Name: *Hydrangea macrophylla*
Varietal Denomination: Strabru

(71) Applicants: Jan van Straaten, Harderwijk (NL); Johan van Straaten, Harderwijk (NL)

(72) Inventors: Jan van Straaten, Harderwijk (NL); Johan van Straaten, Harderwijk (NL)

( * ) Notice: Subject to any disclaimer, the term of this patent is extended or adjusted under 35 U.S.C. 154(b) by 0 days. days.

(21) Appl. No.: 15/530,718

(22) Filed: Feb. 21, 2017

(51) Int. Cl.
*A01H 5/02* (2018.01)

(52) U.S. Cl.
USPC ..... Plt./250

(58) Field of Classification Search
USPC ..... Plt./250
See application file for complete search history.

(56) References Cited

PUBLICATIONS

PLUTO Plant Variety Database Jan. 9, 2018. p. 1.*

* cited by examiner

*Primary Examiner* — Annette H Para
(74) *Attorney, Agent, or Firm* — The Webb Law Firm

(57) ABSTRACT

A new and distinct *Hydrangea* plant having double flowers and dark green leaves.

2 Drawing Sheets

Botanical classification: *Hydrangea macrophylla.*
Varietal denomination: 'STRABRU'.

BACKGROUND OF THE INVENTION

The present invention comprises a new and distinct cultivar of *Hydrangea* plant known by the varietal name 'Strabru'. The new variety was discovered in 2010 in a planned breeding program in Ermelo, The Netherlands. The purpose of the breeding program was to develop unique *Hydrangeas* with double flowers. The new variety is the result of a cross between breeding selection Seedling 08003-2 (female parent, unpatented) and Seedling 10014-6 (male parent, unpatented). The compact nature of 'Strabru' is similar to its female parent, but it differs from Seedling 08003-2 in leaf color and exhibition of double flowers. The bright flower color of 'Strabru' is similar to its male parent, but it differs from Seedling 08003-2 in its exhibition of double flowers. Further, when compared to *Hydrangea* plant named 'Côte d'Azur' (unpatented), 'Strabru' is similar to 'Côte d'Azur' in leaf color and its compact nature. However, 'Strabru' differs from 'Côte d'Azur' in flower color and its exhibition of double flowers. The new variety was first asexually reproduced in 2012 via propagation by cuttings in Ermelo, The Netherlands. The new variety has been trial and field tested in Ermelo, The Netherlands and has been found to retain its distinctive characteristics and remain true to type through successive propagations.

The following traits distinguish 'Strabru' as a new and distinct cultivar from other *Hydrangea* varieties known to the breeder:

1. Exhibition of double flowers; and
2. Dark green leaf color.

DESCRIPTION OF THE DRAWINGS

The accompanying photographic drawings illustrate the new variety at two years old, with the color being as nearly true as is possible with color illustrations of this type.

DESCRIPTION OF THE PLANT

Figure 1:
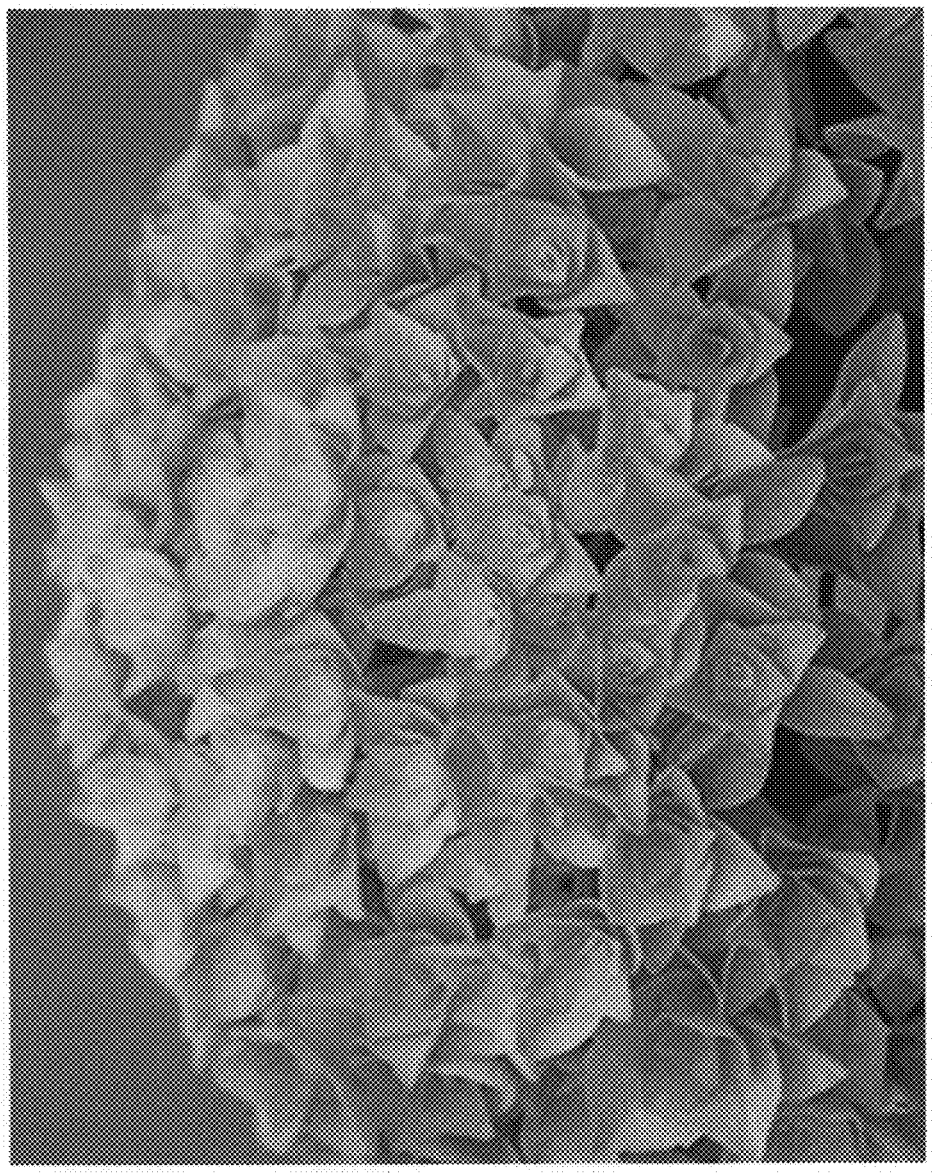
FIG. 1 is close-up photograph of the flowers of the new variety.
Figure 2:
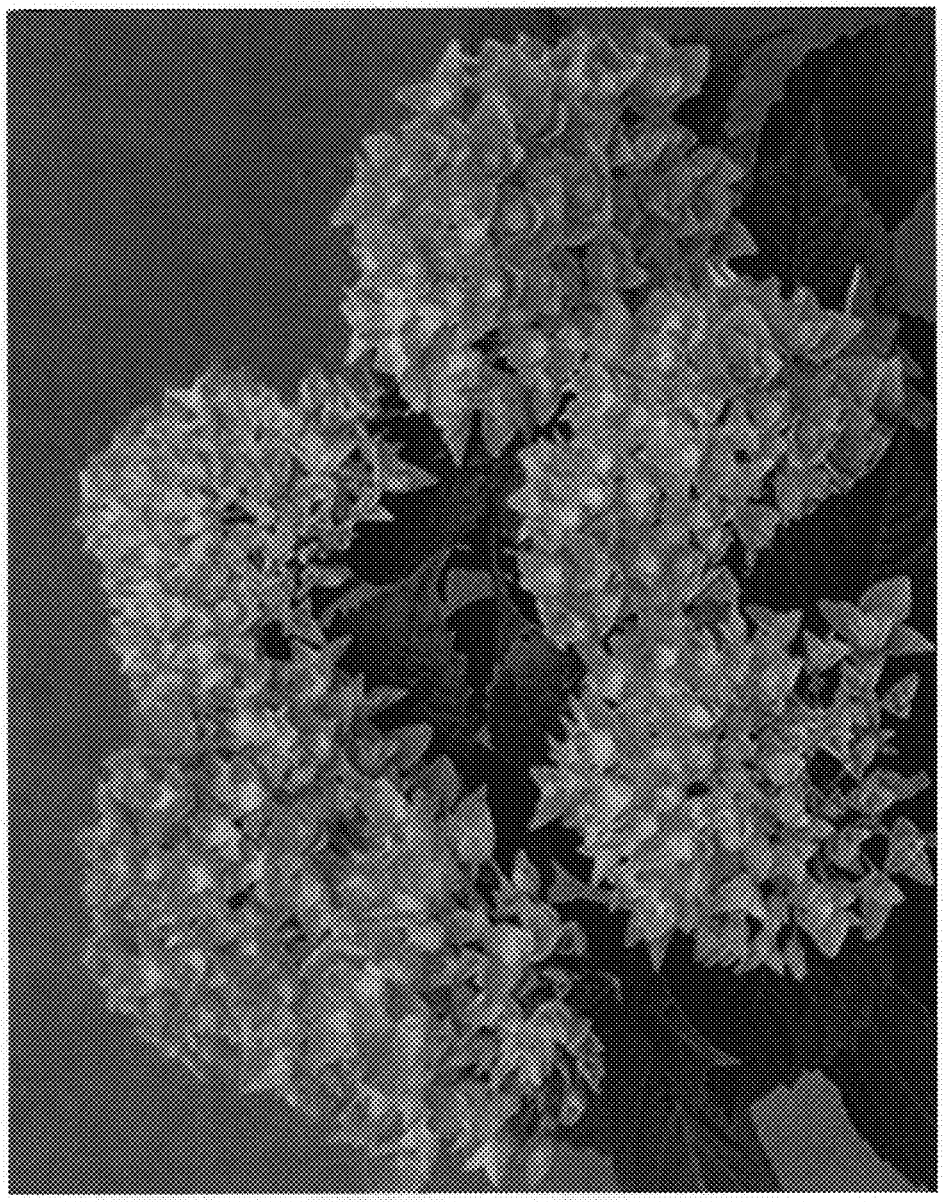
FIG. 2 is another photograph of the same plant of the new variety of FIG. 1, whereby color differences of the flowers are due to differences in the flowering stage of the plant.

The following detailed description sets forth characteristics of the new cultivar. The plants were grown in 15 cm. pots, 8 plants per $m^2$, in ordinary potting soil with granulated fertilizers at a pH of 6.0. The plants were two years old when described. Measurements and color readings of the plants were taken in Ermelo, The Netherlands under natural light. Color references are primarily to the HTML Color Chart.

PLANT

Time to initiate roots: About 14 days at 22° C.
Time to develop roots: About 22 days at 18-20° C.
Rooting habit: Moderate.
Time to produce a finished flowering plant from a rooted cutting: About 48 weeks in a 15 cm container.
Form: Mounded.
Height (from media surface to top of foliage): 35-40 cm.
Height (from media surface to top of flowers): 40-45 cm.
Plant diameter: 35-40 cm.
Vigor: Good.
Strength: Good; no need for artificial support.
Branching habit: Moderately-branched.
Trunk:
*Main trunk length.*—8 cm.
*Diameter.*—1 cm.
*Color.*—Olive Drab 6B 8E 23.
*Texture.*—Shiny.
*Pubescence.*—Absent.
*Internode length.*—1.5-2 cm.

Lateral branches:
*Length*.—Young: 5-10 cm. Mature: 20-25 cm.
*Diameter*.—Young: 0.5 cm. Mature: 0.5 cm.
*Internode length*.—6 cm.
*Texture*.—Shiny.
*Pubescence*.—Absent.
*Color*.—Young: Chartreuse 7F FF 00. Mature: Dark Green 00 64 00.

Foliage:
*Arrangement*.—Single.
*Stipules*.—None present.
*Size of leaf*.—Length: 10 cm. Width: 5-6 cm.
*Shape of leaf* (*generally*).—Young: Elliptic/obtuse. Mature: Elliptic/obtuse.
*Shape of apex*.—Lanceolate.
*Shape of base*.—Round.
*Texture*.—Shiny.
*Aspect*.—V-formed.
*Margin type*.—Serrate.
*Pubescence*.—None present.
*Color*.—Young leaves: Upper surface: Forest Green 22 8B 22. Lower surface: Forest Green 22 8B 22. Mature leaves: Upper surface: Dark Green 00 64 00. Lower surface: Dark Green 00 64 00.
*Petiole*.—Shape: Square. Length: 2 cm. Diameter: 0.5 cm. Color: Olive Drab 6B 8E 23.
*Veins*.—Type: Cross-venulate. Color: Upper surface: Olive 80 80 00. Lower surface: Olive 80 80 00.

FLOWER

Natural flowering season: May until October in Harderwijk, The Netherlands.

Blooming habit: Continuous from late spring through summer.

Bud (measurements made when cluster size was 3 cm):
*Shape of cluster*.—Round.
*Diameter of cluster*.—3 cm.
*Number of buds per cluster*.—40-50.
*Shape*.—Ball.
*Length*.—0.3 cm.
*Width*.—0.3 cm.

Inflorescence:
*Shape*.—Round.
*Length*.—16-20 cm.
*Diameter*.—16-20 cm.
*Average number of flowers per inflorescence*.—50-60.
*Typical number of inflorescences per plant*.—5.
*Lastingness of an individual flower*.—8 weeks.
*Lastingness of an inflorescence*.—8 weeks.

Petals: Absent — the flowerheads are composed of florets that have petaloid sepals (pseudo-sepals) that look like petals.

Petaloids: Absent because of the exhibition of double flowers.

Petaloid sepals (decorative flowers):
*Quantity*.—9-10.
*Overall appearance*.—Pointed and unfused.
*Apex*.—Triangular.
*Base*.—Flat.
*Margin*.—Entire.
*Length*.—2 cm.
*Width*.—3 cm.
*Color*.—Hot Pink FF 69 B4.
*Texture*.—Shiny.

Pedicels:
*Length*.—2 cm.
*Diameter*.—0.2 cm.
*Color*.—Multicolored; Hot Pink FF 69 B4 and Olive 80 80 00.

Peduncles:
*Length*.—3-4 cm.
*Diameter*.—0.3-0.4 cm.
*Texture*.—Smooth.
*Color*.—Olive 80 80 00.

Reproductive organs: Absent because of the exhibition of double flowers.

We claim:

1. A new and distinct variety of *Hydrangea* plant substantially as shown and described herein.

* * * * *